United States Patent [19]

Mewshaw et al.

[11] Patent Number: 5,391,571
[45] Date of Patent: Feb. 21, 1995

[54] CHOLESTEROL ESTER HYDROLASE INHIBITORS

[75] Inventors: Richard E. Mewshaw, Baltimore, Md.; Thomas J. Commons, Wayne; Donald P. Strike, St. Davids, both of Pa.

[73] Assignee: American Home Products Corporation, Madison, N.J.

[21] Appl. No.: 62,026

[22] Filed: May 13, 1993

Related U.S. Application Data

[63] Continuation of Ser. No. 771,580, Oct. 4, 1991, abandoned, which is a continuation of Ser. No. 594,241, Oct. 9, 1990, abandoned, which is a continuation-in-part of Ser. No. 436,841, Nov. 15, 1989, abandoned.

[51] Int. Cl.$^6$ ............... A61K 31/325; C07C 271/02; C07C 271/40
[52] U.S. Cl. .................... 514/490; 514/529; 514/550; 560/20; 560/23; 560/24; 560/29; 560/30; 560/31; 560/32; 560/33; 560/115; 560/117; 560/118; 560/120; 560/121; 560/123; 560/124; 560/133
[58] Field of Search ............. 514/490, 529, 580; 560/20, 23, 24, 29, 30, 31, 32, 33, 115, 117, 118, 120, 121, 123, 124, 133

[56] References Cited

U.S. PATENT DOCUMENTS 4,163,861  8/1979  Illuminati et al. .................. 560/132

FOREIGN PATENT DOCUMENTS 0078099  5/1983  European Pat. Off. .
2612186  9/1988  France .
1592011  7/1981  United Kingdom .

OTHER PUBLICATIONS

Chemical Abstract, vol. 95, #168777u, 1981.
Foldes et al, Experimental Therap. 457–468, 1958.
Bhat et al., Biochem. Biophys. Res. Commun., 109, 486 (1982).
Gallo et al., J. Lipid Research, 25, 604 (1984).
Hosie et al., J. Biol. Chem. 262, 260 (1987).
Stout et al., Biochem. Biophys. Acta, 837, 6 (1985).
Field, J. Lipid Research, 25, 389 (1984).
Cayen et al., J. Lipid Research, 20, 162 (1979).
Foldes et al., J. Pharmacol. Exptl. Therap. 122, 457–464 (1958).
Sumida et al., Plant & Cell Physiol. 14, 781–785 (1973).
van den Berg et al., Pestic. Sci. 13, 29–38 (1982).
Derwent Abstract 81-55962-D of Japanese Patent J56071-058, 1981.

*Primary Examiner*—Mukund J. Shah
*Assistant Examiner*—Y. N. Gupta
*Attorney, Agent, or Firm*—Richard K. Jackson

[57] ABSTRACT

The compounds of the formula:

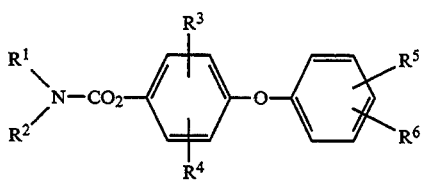

in which $R^1$ is alkyl of 4 or more carbon atoms, cycloalkyl, 1-adamantyl, 2-adamantyl, 3-noradamantyl, 3-methyl-1-adamantyl, 1-fluorenyl, 9-fluorenyl, cycloalkylalkyl, phenyl, substituted phenyl, alkyl, alkoxy, halo, nitro, cyano or trifluoromethyl, phenylalkyl or substituted phenylalkyl, where the substituent on the benzene ring is alkyl, alkoxy, halo, nitro, cyano, trifluoromethyl or phenyl; $R^2$ is hydrogen, alkyl or $R^1$ taken with $R^2$ and the nitrogen atom to which they are attached form a heterocyclic moiety of the formula:

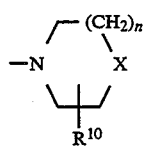

wherein (Abstract continued on next page.)

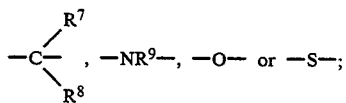

in which $R^7$ is hydrogen, alkyl, hydroxy, alkanoyloxy, hydroxyalkyl, hydroxycarbonyl, alkoxycarbonyl, phenyl or substituted phenyl, in which the substituent is alkyl, alkoxy, halo, nitro, cyano, haloalkyl, perhaloalkyl or dialkylaminoalkyl; $R^8$ is hydrogen or alkyl or $R^7$ and $R^8$ taken together are polymethylene; $R^9$ is hydrogen, alkyl, phenyl or substituted phenyl, in which the substituent is alkyl, alkoxy, halo, nitro, cyano or perhaloalkyl; $R^{10}$ is hydrogen, alkyl or gemdialkyl; n is one of the integers 0, 1 or 2; and $R^3$, $R^4$, $R^5$ and $R^6$ are, independently, hydrogen, alkyl, alkoxy, halo, nitro, cyano or perhaloalkyl, alkoxycarbonyl or hydroxycarbonyl; and when X is $-NR^9-$ or $R^7$ is an amino alkyl group, a pharmaceutically acceptable salt thereof; useful as inhibitors of cholesterol ester hydrolase.

38 Claims, No Drawings

CHOLESTEROL ESTER HYDROLASE INHIBITORS

This is a continuation of Ser. No. 07/771,580, filed Oct. 4, 1991, now abandoned, which is a continuation of Ser. No. 07/594,241, filed Oct. 9, 1990, now abandoned, which is a continuation-in-part of Ser. No. 07/436,841, filed Nov. 15, 1989, now abandoned.

BACKGROUND OF THE INVENTION

Full absorption of dietary cholesterol into the bloodstream is dependent upon cholesterol esterase (cholesterol ester hydrolase; CEH) activity. Bhat et al., Biochem. Biophys. Res. Commun. 109 486 (1982); Gallo et al. J. Lipid Research 25 604 (1984). The removal of cholesterol esterase from pancreatic juice results in an eighty percent reduction in absorbed cholesterol. By inhibiting the action of cholesterol esterase, serum cholesterol levels can be beneficially controlled.

Hosie et at., J. Biological Chem. 262 260 (1987) discusses the irreversible inhibition of cholesterol esterase by p-nitrophenyl N-alkyl carbamates and the reversible inhibition of cholesterol esterase by cholesterol-N-alkyl carbamates.

DESCRIPTION OF THE INVENTION

In accordance with this invention, there is provided a group of novel carbamate esters which are cholesterol ester hydrolase inhibitors. The compounds of this invention present the structural formula:

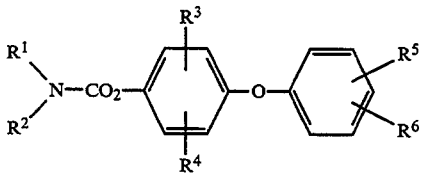

in which $R^1$ is branched or straight chain, saturated or unsaturated alkyl of 4 to 20 carbon atoms, cycloalkyl of 3 to 8 carbon atoms, 1-adamantyl, 2-adamantyl, 3-noradamantyl, 3-methyl-1-adamantyl, 1-fluorenyl, 9-fluorenyl, cycloalkylalkyl where the cycloalkyl moiety has 3 to 8 carbon atoms and the alkyl moiety has 1 to 6 carbon atoms, phenyl, substituted phenyl where the substituents are alkyl of 1 to 6 carbon atoms, alkoxy of 1 to 6 carbon atoms, halo, nitro, cyano or trifluoromethyl, phenylalkyl of 7 to 26 carbon atoms or substituted phenylalkyl, where the alkyl moiety is 1 to 20 carbon atoms and the substituent on the benzene ring is alkyl of 1 to 6 carbon atoms, alkoxy of 1 to 6 carbon atoms, halo, nitro, cyano, trifluoromethyl or phenyl;

$R^2$ is hydrogen, alkyl of 1 to 6 carbon atoms or $R^1$ taken with $R^2$ and the nitrogen atom to which they are attached form a heterocyclic moiety of the formula:

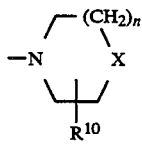

wherein

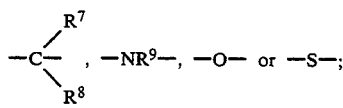

in which $R^7$ is hydrogen, branched or straight chain alkyl of 1 to 6 carbon atoms, hydroxy, alkanoyloxy of 2 to 6 carbon atoms, hydroxyalkyl of 1 to 6 carbon atoms, hydroxycarbonyl, alkoxycarbonyl of 2 to 16 carbon atoms, phenyl or substituted phenyl in which the substituent is alkyl of 1 to 6 carbon atoms, alkoxy of 1 to 6 carbon atoms, halo, nitro, cyano, haloalkyl of 1 to 6 carbon atoms, perhaloalkyl of 1 to 6 carbon atoms or dialkylaminoalkyl in which each alkyl group contains from 1 to 6 carbon atoms;

$R^8$ is hydrogen or branched or straight chain alkyl of 1 to 6 carbon atoms or $R^7$ and $R^8$ taken together are polymethylene of 2 to 6 carbon atoms;

$R^9$ is hydrogen, alkyl of 1 to 6 carbon atoms, phenyl or substituted phenyl in which the substituent is alkyl of 1 to 6 carbon atoms, alkoxy of 1 to 6 carbon atoms, halo, nitro, cyano or perhaloalkyl of 1 to 6 carbon atoms;

R10 is hydrogen, alkyl of 1 to 6 carbon atoms or gemdialkyl of 2 to 12 carbon atoms;

n is one of the integers 0, 1 or 2;

and $R^3$, $R^4$, $R^5$ and $R^6$ are, independently, hydrogen, branched or straight chain alkyl of 1 to 6 carbon atoms, alkoxy of 1 to 6 carbon atoms, halo, nitro, cyano or perhaloalkyl of 1 to 6 carbon atoms, alkoxycarbonyl of 2 to 16 carbon atoms or hydroxycarbonyl;

and when X is $-NR^9-$ or $R^7$ is an amino alkyl group, a pharmaceutically acceptable salt thereof.

The preferred compounds of this invention, based upon their in vitro cholesterol esterase inhibitory properties, are those of the formula:

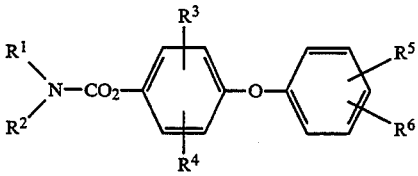

in which $R^1$ is branched or straight chain alkyl of 4 to 20 carbon atoms, cycloalkyl of 4, 5, 6 or 7 carbon atoms, cycloalkylalkyl of 6 to 8 carbon atoms, phenylalkyl of 7 to 26 carbon atoms;

$R^2$ is hydrogen, methyl, ethyl or $R^1$ and $R^2$ taken together with the nitrogen atom to which they are attached form a heterocyclic moiety of the formula:

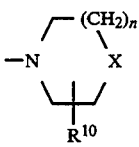

wherein

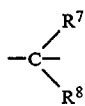

in which

R$^7$ is hydrogen, branched or straight chain alkyl of 1 to 6 carbon atoms, hydroxy, hydroxyalkyl of 1 to 6 carbon atoms, alkanoyloxy of 2 to 6 carbon atoms, hydroxycarbonyl, alkoxycarbonyl of 2 to 6 carbon atoms, phenyl or substituted phenyl in which the substituent is alkyl o#1 to 6 carbon atoms, alkoxy of 1 to 6 carbon atoms, halo, nitro, cyano, haloalkyl of 1 to 6 carbon atoms or perhaloalkyl of 1 to 6 carbon atoms;

R$^8$ is hydrogen or branched or straight chain alkyl of 1 to 6 carbon atoms or R$^7$ and R$^8$ taken together are polymethylene of 2 to 6 carbon atoms;

R$^{10}$ is hydrogen, alkyl of 1 to 6 carbon atoms or gem-dialkyl of 2 to 12 carbon atoms;

n is one of the integers 0, 1 or 2; and

R$^3$, R$^4$, R$^5$ and R$^6$ are, independently, hydrogen, alkyl of 1 to 6 carbon atoms, alkoxy of 1 to 6 carbon atoms, nitro, halo, alkoxycarbonyl of 2 to 16 carbon atoms, hydroxycarbonyl, cyano or trihalomethyl.

In the description of the compounds of this invention, by halo, applicants mean chloro, bromo, iodo or fluoro. The perhaloalkyl substituents are preferably perfluoroalkyl and the alkyl and alkoxy substituents preferably have from 1 to 4 carbon atoms.

The novel carbamate esters provided by the present invention can be prepared by the following process in which the symbol R$^{11}$ will be used to represent a group having the formula A.

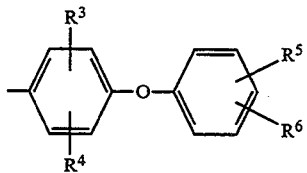

The present invention provides a process for the preparation of a carbamate ester having the formula R$^1$R$^2$N—CO—O—R$^{11}$ where R$^1$, R$^2$ and R$^{11}$ are as defined above or a pharmaceutically acceptable salt thereof, wherein:

(a) a phenol having the formula R$^{11}$OH, where R$^{11}$ is as defined above, is reacted with a carbamoylating agent to introduce a carbamoyl group having the formula R$^1$R$^2$N—CO— at the phenolic oxygen atom wherein R$^1$ and R$^2$ are as defined above subject to the proviso that where X is —CR$^8$(OH)— or —NH— in the carbamate ester, the alcoholic oxygen atom or amine nitrogen atom of X in the carbamoylating agent may be protected against carbamoylation with a removable protecting group; or (b) an amine having the formula R$^1$R$^2$NH, where R$^1$ and R$^2$ are as defined in respect of the carbamate ester except that, where X represents —CR$^8$(OH)— or —NH— in the carbamate ester, then the alcoholic oxygen atom or the amine nitrogen atom of X may be protected against phenoxycarbonylation by protection with a removable protecting group, is reacted with a phenoxycarbonylating agent for introducing a substituted phenoxycarbonyl group having the formula —CO—OR$^{11}$ where R$^{11}$ is as defined above; and, if appropriate, a removable protecting group is removed and, if desired, a free base form of the carbamate ester where X is —NR$^9$— may be converted into a pharmaceutically acceptable acid addition salt thereof by addition of an acid.

The carbamoylation of a phenol may be carried out in a solvent such as methylene chloride. A tertiary amine, for example, triethylamine, may be included in the reaction mixture as a catalyst. As carbamoylating agent there is preferably used an isocyanate having the formula R$^1$-NCO where R$^1$ is as defined above. In this case, R$^2$ is hydrogen in the carbamate ester obtained as product.

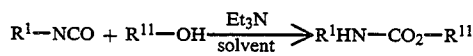

As an alternative to the isocyanate, a carbamoyl halide of the formula R$^1$R$^2$N—CO—Hal where R$^1$ and R$^2$ are as defined above and Hal is halogen, preferably chlorine, may be employed as carbamoylating agent.

The isocyanate reactant may be prepared by reacting a primary amine having the formula R$^1$NH$_2$ where R$^1$ is as defined above with phosgene. A substantial excess

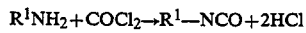

of the amine should normally be avoided since it may lead to the formation of a urea derivative (R$^1$—N-H—)$_2$CO as by-product. The reaction of the primary amine R$^1$NH$_2$ with phosgene may yield the N-monosubstituted carbamoyl chloride R$^1$HN—COCl but, if so, this product tends to be unstable and to dissociate into the isocyanate R$^1$—NCO and hydrogen chloride. The N,N-disubstituted carbamoyl chlorides, i.e. the compounds R$^1$R$^2$N—CO—Hal where R$^2$ is other than hydrogen, can be prepared by reacting a secondary amine R$^1$R$^2$NH with phosgene.

The carbamate ester of the present invention may also be prepared by phenoxycarbonylation of a primary or secondary amine R$^1$R$^2$NH. As phenoxycarbonylating agent there is preferably used the chloroformate ester of the appropriate phenol. The chloroformam ester can be prepared by reacting the phenol R$^{11}$OH with phosgene or by reaction with trichloromethyl chloroformate.

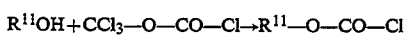

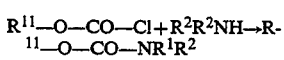

Where it is intended to prepare an end compound in which the symbol X represents —CR$^8$(OH)— or —NH—, protection of the alcoholic hydroxyl group or the amine nitrogen atom of X is advisable to prevent undesired reaction at the wrong location. The books entitled "Protective Groups In Organic Chemistry", J. F. W. McOmie (ed.), Plenum Press, London and New York (1973) and "Protective Groups in Organic Synthesis", T. W. Greene, John Wiley & Sons, New York (1981) provide many examples of protecting groups that may be used. Of course, the protecting group should be so selected that it can be removed from the phenoxycarbonylation product or carbamoylation product under conditions in which the carbamate ester desired as end compound can survive. In particular, it should be noted that the carbamate esters may react with nucleophiles under basic conditions and thus such reaction conditions are best avoided for removing the protecting group. As an example of a synthesis, secondary amines having the formula B or C

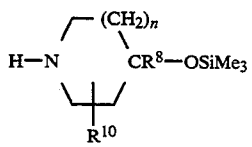

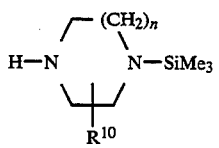

may be aryloxycarbonylated with a chloroformate ester of an appropriate p-phenoxyphenol and the resultant carbamates having the formula D or E

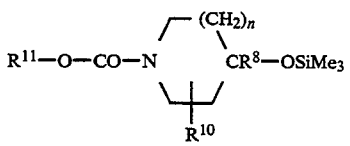

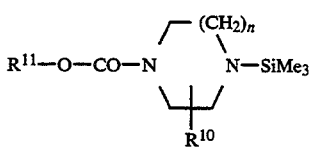

are converted into the compounds F or G by hydrolysis during work up of the reaction mixture.

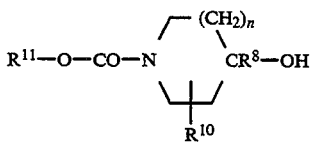

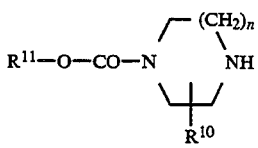

The novel carbamates of the present invention where $R^1$ and $R^2$ includes $-NR^9-$ as X are basic compounds which can be convened into pharmaceutically acceptable acid addition salts by addition of an acid. The salt may be derived from such organic and inorganic acids as lactic, acetic, citric, tartaric, succinic, maleic, fumaric, malonic, gluconic, hydrochloric, hydrobromic, phosphoric, nitric, sulphuric and methanesulphonic and similarly known acceptable acids.

The invention also provides a pharmaceutical composition comprising a new carbamate ester according to the invention or a pharmaceutically acceptable salt thereof in association or combination with a pharmaceutically acceptable carrier and a method of making such a composition by bringing the carbamate ester or its pharmaceutically acceptable salt into association or combination with the carrier.

EXAMPLE 1

Butylcarbamic acid 4-phenoxyphenyl ester

Triethylamine (15 ml, 0.11 mol) was added dropwise under a nitrogen atmosphere to a solution of 4-phenoxyphenol (25.1 g, 0.14 mol) and butyl isocyanate (18 ml, 0.16 mol) in 400 ml of methylene chloride. After the addition, the solution was stirred overnight at room temperature. The solution was extracted with 1 N HCl, dried (MgSO$_4$) and the solvent removed under reduced pressure to give 39.59 g of a tan solid. Recrystallization from diisopropyl ether gave the title compound as a white crystalline solid (21.01 g, 55%), mp 75°-77° C.

Elemental analysis for $C_{17}H_{19}NO_3$ Calc'd: C, 71.56; H, 6.71; N, 4.91 Found: C, 71.78; H, 6.80; N, 5.06

EXAMPLE 2

1-Piperidinecarboxylic acid 4-phenoxyphenyl ester

A solution of 4-phenoxyphenol (5.0 g, 26.9 mmol) and dimethylaniline (3.4 ml, 26.8 mmol) in 35 ml of benzene plus 1.5 ml of dioxane was added dropwise over 15 minutes under a nitrogen atmosphere to a solution of trichloromethyl chloroformate (1.6 ml, 13.3 mmol) in 30 ml of benzene at ice bath temperature. After the addition, the cooling bath was removed and the stirring continued for 24 hours. The reaction was cooled to ice bath temperature and a solution of piperidine (2.7 ml, 27.3 mmol) and pyridine (4.4 ml, 54.4 mmol) in 20 ml of benzene was added dropwise over 15 minutes. After the addition, the reaction was stirred at ice bath temperature for 3 hours. The cooling bath was removed and the stirring continued for 22 hours. The reaction was diluted with benzene and extracted two times with 1 N HCl. The organic solution was dried over anhydrous MgSO$_4$ and the solvent was removed under reduced pressure to give 7.21 g of an oil. Purification by HPLC (hexane:EtOAc) gave 5.05 g of a light yellow crystalline solid. Recrystallization from diisopropyl ether gave the title compound as a white crystalline solid (3.11 g, 39%), mp 74°-76° C.

Elemental analysis for $C_{18}H_{19}NO_3$ Calc'd: C, 72.71; H, 6.44; N, 4.71 Found: C, 72.40; H, 6.42; N, 4.78

EXAMPLE 3

(4-Phenylbutyl)carbamic acid 4-phenoxyphenyl ester

In the same manner as described in Example 2, the title compound was produced as a white crystalline solid (3.11 g, 33%), mp 104°-105° C.

Elemental analysis for $C_{23}H_{23}NO_3$ Calc'd: C, 76.43; H, 6.41; N, 3.88 Found: C, 76.13; H, 6.28; N, 3.88

EXAMPLE 4

(1,5-Dimethylhexyl)carbamic acid 4-phenoxyphenyl ester

In the same manner as described in Example 2, the title compound was produced as a white crystalline solid (4.0 g, 44%), mp 64°-65° C.

Elemental analysis for $C_{21}H_{27}NO_3$ Calc'd: C, 73.87; H, 7.97; N, 4.10 Found: C, 74.19; H, 7.77; N, 3.85

EXAMPLE 5

4-Phenyl1-piperidinecarboxylic acid 4-phenoxyphenl ester

In the same manner as described in Example 2, the title compound was produced as white crystalline solid (4.20 g, 42%), mp 122°–124° C.

Elemental analysis for $C_{24}H_{23}NO_3$ Calc'd: C, 77.19; H, 6.21; N, 3.75 Found: C, 77.04; H, 6.17; N, 4.12

EXAMPLE 6

4-Phenyl-1-piperazinecarboxylic acid 4-phenoxyphenyl ester

In the same manner as described in Example 2, the title compound was produced as a white crystalline solid (4.68 g, 47%), mp 159°–161° C.

Elemental analysis for $C_{23}H_{22}N_2O_3$ Calc'd: C, 73.78; H, 5.92; N, 7.48 Found: C, 73.47: H, 5.85; N, 7.37

EXAMPLE 7

4-Morpholinecarboxylic acid 4-phenoxyphenol ester

In the same manner as described in Example 2, the title compound was produced as a white crystalline solid (4.07 g, 51% ), mp 95°–96° C.

Elemental analysis for $C_{17}H_{17}NO_4$ Calc'd: C, 68.22; H, 5.72; N, 4.68 Found: C, 67.96; H, 5.93; N, 4.63

EXAMPLE 8

4-Methyl-1-piperidinecarboxylic acid 4-phenoxyphenyl ester

In the same manner as described in Example 2, the title compound was produced as a white crystalline solid (3.88 g, 46%), mp 47°–49° C.

Elemental analysis for $C_{19}H_{21}NO_3$ Calc'd: C, 73.29; H, 6.80; N, 4.50 Found: C, 73.40; H, 7.09; N, 4.53

EXAMPLE 9

4-Methyl-1-piperazinecarboxylic acid 4-phenoxyphenyl ester

In the same manner as described in Example 2, with the exception that upon extracting with 1N HCl an emulsion formed which was broken by basifying with 5% $NaHCO_3$. After further work-up, as described in Example 2, the title compound was produced as a white crystalline solid (5.21 g, 62%), mp 79°–81° C.

Elemental analysis for $C_{18}H_{20}N_2O_3$ Calc'd: C, 69.21; H, 6.45; N, 8.97 Found: C, 69.11; H, 6.79; N, 8.84

EXAMPLE 10

4-Thiomorpholinecarboxylic acid 4-phenoxyphenyl ester

In the same manner as described in Example 2, the title compound was produced as a white crystalline solid (5.01 g, 59%), mp 101°–103° C.

Elemental analysis for $C_{17}H_{17}NO_3S$ Calc'd: C, 64.74; H, 5.43; N, 4.44 Found: C, 64.96; H, 5.46; N, 4.50

EXAMPLE 11

Octylcarbamic acid 4phenoxyphenyl ester

In the same manner as described in Example 1, the title compound was produced as a white crystalline solid after purification by column chromatography (silica gel, 230–400 mesh) using 8:1 hexane: ethyl acetate as an eluent (8.10 g, 88%), mp 44°–46° C.

Elemental analysis for $C_{21}H_{27}NO_3$ Calc'd: C, 73.87; H, 7.97; N, 4.10 Found: C, 73.90; H, 8.01; N, 4.19

EXAMPLE 12

1-Pyrrolidinecarboxylic acid 4-phenoxyphenyl ester

In the same manner as described in Example 2, the title compound was produced as a white crystalline solid (4.43 g, 58%), mp 53°–55° C.

Elemental analysis for $C_{17}H_{17}NO_3$ Calc'd: C, 72.07; H, 6.05; N, 4.94 Found: C, 71.97; H, 6.30; N, 4.77

EXAMPLE 13

Cyclohexylcarbamic acid 4-phenoxyphenyl ester

In the same manner as described in Example 1, the title compound was produced as a white crystalline solid after recrystallization of the crude reaction product from isopropanol (7.51 g, 90% ), mp 166°–168° C.

Elemental analysis for $C_{19}H_{21}NO_3$ Calc'd: C, 73.29; H, 6.80; N, 4.50 Found: C, 73.18; H, 6.94; N, 4.48

EXAMPLE 14

Cyclohexylmethylcarbamic acid 4phenoxyphenyl ester

In the same manner as described in Example 2, the title compound was produced as a white crystalline solid (3.49 g, 40%), mp 100°–102° C.

Elemental analysis for $C_{20}H_{23}NO_3$ Calc'd: C, 73.82; H, 7.12; N, 4.30 Found: C, 73.79; H, 7.12; N, 4.29

EXAMPLE 15

Tricyclo[3,3,1,1(3.7)dec-1-yl-carbamic acid 4-phenoxyphenyl ester

In the same manner as described in Example 2, the title compound was produced as a white crystalline solid (1.54 g, 16%), mp 145°–147° C.

Elemental analysis for $C_{23}H_{25}NO_3$ Calc'd: C, 76.01; H, 6.93; N, 3.85 Found: C, 76.08; H, 6.91; N, 3.83

EXAMPLE 16

(1,1,3,3-Tetramethylbutyl)carbamic acid 4-phenoxyphenyl ester

In the same manner as described in Example 2, the title compound was produced as a white crystalline solid (2.0 g, 22%), mp 70°–71 ° C.

Elemental analysis for $C_{21}H_{27}NO_3$ Calc'd: C, 73.87; H, 7.97; N, 4.10 Found: C, 73.80; H, 7.94; N, 4.10

EXAMPLE 17

(1-Ethylpentyl)carbamic acid 4-phenoxyphenyl ester

In the same manner as described in Example 2, the title compound was produced as a white crystalline solid (2.87 g, 33%), mp 70°–72° C.

Elemental analysis for $C_{20}H_{25}NO_3$ Calc'd: C, 73.37; H, 7.70; N, 4.28 Found: C, 73.30; H, 7.67; N, 4.24

EXAMPLE 18

(1,3-Dimethylbutyl)carbamic acid 4phenoxyphenyl ester

In the same manner as described in Example 2, the title compound was produced as a white crystalline solid (5.03 g, 60%), mp 71°–74° C.

Elemental analysis for $C_{19}H_{23}NO_3$ Calc'd: C, 72.82; H, 7.40; N, 4.47 Found: C, 72.78; H, 7.45; N, 4.39

EXAMPLE 19

Butylcarbamic acid 4-(4-methylphenoxy)phenyl ester

A mixture of p-cresol (41.8 ml, 0.4 mol) and sodium methoxide (21.2 g, 0.4 mol) in 400 ml of anhydrous pyridine was refluxed with stirring under nitrogen for 1 hour. The methanol was distilled off. After cooling to room temperature 4-bromoanisole (49.1 ml, 0.4 mol) and copper (I) chloride (6 g, 0.06 mol) were added and the mixture refluxed for 17 hours. Most of the pyridine was removed by distillation. The residue was poured into water, acidified with dilute HCl (1:1 conc. HCl:H$_2$O) and extracted with methylene chloride. The organic layer was extracted two times with 1 N NaOH, dried (MgSO$_4$) and the solvent removed under reduced pressure to give a brown solid. Purification by HPLC (hexane-methylene chloride) gave 4methoxy-4′-methyl-diphenyl ether as a light tan crystalline solid (73.47 g, 88%), mp 39°–44° C.

Elemental analysis for $C_{14}H_{14}O_2$ Calc'd: C, 78.48; H, 6.59 Found: C, 78.22; H, 6.67

4-Methoxy-4′-methyl-diphenyl ether (25 g, 0.12 mol) was dissolved in 120 ml of glacial acetic acid and then treated with 100 ml of 48% HBr. The mixture was heated to reflux during which time everything dissolved. The resulting solution was refluxed for 4.5 hours. The reaction mixture was poured into ice water and extracted three times with methylene chloride. The combined organic extracts were washed five times with water, dried (MgSO$_4$) and the solvent removed under reduced pressure to give a brown solid. Purification by HPLC (hexane-methylene chloride) gave 4-hydroxy-4′-methyldiphenyl ether as an off-white crystalline solid (19.50 g, 83%), mp 74°–76° C.

Elemental analysis for $C_{13}H_{12}O_2$ Calc'd: C, 77.98; H, 6.04 Found: C, 78.31; H, 6.13

In the same manner as described in Example 1, the title compound was produced from the intermediate prepared in the preceding paragraph as a white crystalline solid after recrystallization of the crude reaction product from hexanediisopropyl ether (4.99 g, 67%), mp 64°–66° C.

Elemental analysis for $C_{18}H_{21}NO_3$ Calc'd: C, 72.22; H, 7.07; N, 4.68 Found: C, 72.61; H, 7.13; N, 4.79

EXAMPLE 20

Butylcarbamic acid 4-(4-nitrophenoxy)phenyl ester

4-Methoxyphenol (25 g, 0.20 mol) was heated under a nitrogen atmosphere to 70° C. during which time the solid melted. Eighty-five percent potassium hydroxide (12.4 g, 0.19 mol) was added all at once and the mixture stirred at 70° C. for 1 hour. 1-Bromo-4-nitrobenzene (33 g, 0.16 mol) and copper powder (0.1 g, 1.57 mmol) were added and the mixture stirred at 190° C. for 3 hours. After cooling to room temperature, the residue was partitioned between benzene and water. The organic layer was then extracted two times with 5% KOH, dried (MgSO$_4$) and the solvent removed under reduced pressure to give a brown solid. Purification by HPLC (hexane-methylene chloride) gave 4-methoxy-4′-nitrodiphenyl ether as a yellow crystalline solid (19.05 g, 49%), mp 107°–109° C.

Elemental analysis for $C_{13}H_{11}NO_4$ Calc'd: C, 63.67; H, 4.52; N, 5.71 Found: C, 64.00; H, 4.43; N, 5.85

A suspension of 4-methoxy-4′-nitrodiphenyl ether (5.0 g, 20.4 mmol) in 25 ml of glacial acetic acid plus 20 ml of 48% HBr was heated under a nitrogen atmosphere to reflux temperature. During this time, everything dissolved. The solution was then. refluxed for 3 hours. Upon cooling to room temperature, crystals formed. The crystals were collected by filtration, washed with water and dried under high vacuum to give 4-hydroxy-4′-nitrodiphenyl ether as a yellow crystalline solid (4.34, 92%), mp 168°–172° C.

Elemental analysis for $C_{12}H_9NO_4$ Calc'd: C, 62.34; H, 3.92; N, 6.06 Found: C, 62.01; H, 3.93; N, 6.09

In the same manner as described in Example 1, the title compound was produced from the intermediate prepared in the preceding paragraph as a light yellow crystalline solid after recrystallization of the crude reaction product from methylene chloride-diisopropyl ether (3.49 g, 71%), mp 122°–124° C.

Elemental analysis for $C_{17}H_{18}N_2O_5$ Calc'd: C, 61.81; H, 5.49; N, 8.48 Found: C, 61.57; H, 5.45; N, 8.29

EXAMPLE 21

Butylcarbamic acid 4-(4-chlorophenoxy)phenyl ester

A mixture of 4-bromoanisole (35 ml, 0.28 mol), 4-chlorophenol (43 g, 0.33 mol), anhydrous K$_2$CO$_3$ (13 g, 0.09 mol) and copper bronze (0.38 g, 5.98 mmol) were stirred under a nitrogen atmosphere at 210° C. for 2 hours. After cooling to room temperature, the mixture was dissolved in methylene chloride, extracted two times with 1 N NaOH, dried (MgSO$_4$) and the solvent removed under reduced pressure to give a brown liquid. Excess 4-bromoanisole was removed by distillation under reduced pressure (60°–73° C., 1 mm) and the residual crystalline solid was purified by HPLC (hexane-methylene chloride). 4-Methoxy-4′-chlorodiphenyl ether was isolated as a white crystalline solid (28.84 g, 44%), mp 49°–51° C.

Elemental analysis for $C_{13}H_{11}ClO_2$ Calc'd: C, 66.53; H, 4.73 Found: C, 66.66; H, 4.82

In the same manner described in the second paragraph of Example 19, 4-hydroxy-4′-chlorodiphenyl ether was produced as a white crystalline solid (16.92 g, 90%), mp 69°–71° C.

Elemental analysis for $C_{12}H_9ClO_2$ Calc'd: C, 65.32; H, 4.11 Found: C, 65.18; H, 4.16

In the same manner as described in Example 1, the title compound was produced from the intermediate of the preceding paragraph as a white crystalline solid after recrystallization of the crude reaction product from diisopropyl ether (4.18 g, 72%), mp 106°–108° C.

Elemental analysis for $C_{17}H_{18}ClNO_3$ Calc'd: C, 63.85; H, 5.67; N, 4.38 Found: C, 63.78; H, 5.78; N, 4.41

EXAMPLE 22

Butylcarbamic acid 2,6-dimethyl-4-(4-methylphenoxy)phenyl ester

In the same manner as described in paragraphs 1 and 2 of Example 19, 4-methoxy-3,4′, 5-trimethyldiphenyl ether was produced as a light yellow oil (23.8 g, 82%). Demethylation gave 4-hydroxy-3,4′, 5-trimethyldiphenyl ether as a white crystalline solid (4.31 g, 46%) after purification by HPLC (methylene:hexane) and recrystallization from hexane, mp 58°–60° C.

Elemental analysis for $C_{15}H_{16}O_2$ Calc'd: C, 78.92; H, 7.06 Found: C, 78.79; H, 7.28

In the same manner as described in Example 1, the title compound was produced from the intermediate prepared in the preceding paragraph as a white crystalline solid after recrystallization of the crude reaction product from diisopropyl ether (3.91 g, 78%), mp 110°–112° C.

Elemental analysis for $C_{20}H_{25}NO_3$ Calc'd: C, 73.37; H, 7.70; N, 4.28 Found: C, 73.06; H, 7.83; N, 4.32

EXAMPLE 23

4-Methyl-1-piperidinecarboxylic acid 4-(4-methylphenoxy)phenyl ester

In the same manner as described in Example 2, the title compound was produced from the intermediate prepared in paragraphs 1 and 2 of Example 19 as a white crystalline solid after recrystallization from diisopropyl ether (1.78 g, 22%), mp 79°–81° C.

Elemental analysis for $C_{20}H_{23}NO_3$ Calc'd: C, 73.82; H, 7.12; N, 4.30 Found: C, 73.78; H, 7.06; N, 4.25

EXAMPLE 24

(1,5-Dimethylhexyl)carbamic acid 4-(4-methylphenoxy)phenyl ester

In the same manner as described in Example 2, the title compound was produced from the intermediate prepared in paragraphs 1 and 2 of Example 19 as a white crystalline solid after recrystallization from hexane (5.16 g, 58%), mp 45°–47° C.

Elemental analysis for $C_{22}H_{29}NO_3$ Calc'd: C, 74.33; H, 8.22; N, 3.94 Found: C, 74.11; H, 8.28; N, 3.84

EXAMPLE 25

4-Methyl-1-piperidinecarboxylic acid 4-(4-chlorophenoxy)phenyl ester

In the same manner as described in Example 2, the title compound was produced from the intermediate prepared in paragraphs 1 and 2 of Example 21 as a white crystalline solid after recrystallization from hexane (3.83 g, 54%), mp 72°–75° C.

Elemental analysis for $C_{19}H_{20}ClNO_3$ Calc'd: C, 65.99; H, 5.83; N, 4.05 Found: C, 65.91; H, 5.86; N, 4.08

EXAMPLE 26

(1-Methylhexyl)carbamic acid 4-phenoxyphenyl ester

In the same manner as described in Example 2, the title compound was produced as a white crystalline solid after recrystallization from hexane (5.38 g, 62%), mp 59°–61° C.

Elemental analysis for $C_{20}H_{25}NO_3$ Calc'd: C, 73.37; H, 7.70; N, 4.28 Found: C, 73.28; H, 7.66; N, 4.37

EXAMPLE 27

(1,5-Dimethylhexyl)carbamic acid 4-(4-chlorophenoxy)phenyl ester

In the same manner as described in Example 2, the title compound was produced from the intermediate prepared in paragraphs 1 and 2 of Example 21 as a white crystalline solid after recrystallization from hexane (4.54 g, 60%), mp 46°–48° C.

Elemental analysis for $C_{21}H_{26}ClNO_3$ Calc'd: C, 67.10; H, 6.97; N, 3.73 Found: C, 67.02; H, 6.94; N, 3.58

EXAMPLE 28

Butylcarbamic acid 2-fluoro-4-phenoxyphenyl ester

A solution of 85% potassium hydroxide (3.88 g, 58.8 mmol) in 3 ml of water was added to a solution of phenol (6.1 g, 64.8 mmol) in 40 ml of toluene. The resulting mixture was refluxed under a nitrogen atmosphere and a Dean-Stark trap for 3.5 hours. After standing overnight at room temperature, the toluene was removed by distillation under reduced pressure and the resulting solid dried under high vacuum. To this solid 4-bromo-2-fluoroanisole (6.4 ml, 49.6 mmol) and copper (1) chloride (0.1 g, 1.0 mmol) were added and the mixture heated at 180° C. for 2 hours. After cooling to room temperature, the mixture was partitioned between diethyl ether and water and extracted. The ether layer was extracted two times with 1N NaOH, dried (MgSO$_4$) and the solvent was removed under reduced pressure to give 9.73 g of a brown oil. Purification of the material by column chromatography (silica gel, 230–400 mesh) using hexane-methylene chloride as the eluent gave 3-fluoro-4-methoxydiphenyl ether as a clear oil (8.56 g, 79%): IR(film) 3080, 3020, 2970, 2940, 2850, 1595, 1510 and 1490 cm$^{-1}$; ms m/e, 218 (m+).

In the same manner as described in the second paragraph of Example 19, 3-fluoro-4-hydroxydiphenyl ether was produced as an oil (6.57 g, 92%): ms m/e, 204 (m+).

Elemental analysis for $C_{12}H_9FO_2$ Calc'd: C, 70.58; H, 4.44 Found: C, 70.24; H, 4.33

In the same manner as described in Example 1, the title compound was produced from the intermediate of the preceding paragraph as an oil after purification by column chromatography (silica gel, 230–400 mesh) using hexane-methylene chloride as an eluent (5.76 g, 97%): ms m/e, 303 (m+).

Elemental analysis for $C_{17}H_{18}FNO_3$ Calc'd: C, 67.32; H, 5.98; N, 4.62 Found: C, 66.94; H, 5.93; N, 4.51

EXAMPLE 29

Butylcarbamic acid 4-(4-methoxyphenoxy)phenyl ester

In the same manner as described in paragraph 1 of Example 19, 4-benzyloxy-4'-methoxydiphenyl ether was produced as a white crystalline solid after trituration with hexane of the HPLC (eluent: hexane-methylene chloride) purified material (24.53 g, 64%), mp 106°–108° C.

Elemental analysis for $C_{20}H_{18}O_3$ Calc'd: C, 78.41; H, 5.92 Found: C, 78.29; H, 5.90

4-Benzyloxy-4'-methoxydiphenyl ether was dissolved in 150 ml of ethyl acetate. To this solution, 2 g of 10% Pd-C was added and the mixture hydrogenated at room temperature and 25 psi for 24 hours. After removal of the catalyst by filtration through celite and removal of the solvent under reduced pressure, 5.63 g of a crystalline solid remained. Recrystallization of this material from diisopropyl etherhexane produced 4-hydroxy-4'-methoxydiphenyl ether as a white crystalline solid (4.74 g, 84%), mp 88°–90° C.

Elemental analysis for $C_{13}H_{12}O_3$ Calc'd: C, 72.21; H, 5.59 Found: C, 72.12; H, 5.29

In the same manner as described in Example 1, the title compound was produced from the intermediate of the preceding paragraph as a white crystalline solid after recrystallization of the crude reaction product from diisopropyl ether (3.85 g, 88%), mp 63°–64° C.

Elemental analysis for $C_{18}H_{21}NO_4$ Calc'd: C, 68.55; H, 6.71; N, 4.44 Found: C, 68.51; H, 6.58; N, 4.52

EXAMPLE 30

4-Methyl-1-piperidinecarboxylic acid 4-(4-methoxyphenoxy)phenyl ester

In the same manner as described in Example 2, the title compound was produced from the intermediate prepared in paragraphs 1 and 2 of Example 29 as a white crystalline solid after recrystallization from diisopropyl ether (3.34 g, 74%), mp 81°–84° C.

Elemental analysis for $C_{20}H_{23}NO_4$ Calc'd: C, 70.36; H, 6.79; N, 4.10 Found: C, 70.33; H, 6.73; N, 3.70

EXAMPLE 31

(1,5-Dimethylhexyl)carbamic acid 4-(4-methoxyphenoxy)phenyl ester

In the same manner as described in Example 2, the title compound was produced from the intermediate prepared in paragraphs 1 and 2 of Example 29 as a white crystalline solid after recrystallization from hexane (0.83 g, 12%), mp 64°–65° C.

Elemental analysis for $C_{22}H_{29}NO_4$ Calc'd: C, 71.13; H, 7.87; N, 3.77 Found: C, 71.14; H, 8.14; N. 3.77

EXAMPLE 32

Butylcarbamic acid 4 -[4-(1,1-dimethylethyl)phenoxy]phenyl ester

In the same manner as described in paragraphs 1 and 2 of Example 19, 4-(1,1-dimethylether)-4'-methoxydiphenyl ether was produced as a light yellow oil (55.95 g, 86%). Demethylation gave 4-(1,1-dimethylether)-4'-methoxydiphenyl ether as a light yellow oil (8.09 g, 68%): IR (film) 3380, 3050, 2970, 2910, 2880, 1605 and 1500 cm$^{-1}$; ms m/e, 242 (m+).

In the same manner as described in Example 1, the title compound was produced from the intermediate in the preceding paragraph as a white crystalline solid after recrystallization of the crude reaction product from hexane (3.62 g, 74%), mp 78°–80° C.

Elemental analysis for $C_{21}H_{27}NO_3$ Calc'd: C, 73.87; H, 7.97; N, 4.10 Found: C, 73.58; H, 7.90; N, 4.08

EXAMPLE 33

Butylcarbamic acid 2-bromo-4-phenoxyphenyl ester

Bromine (21.0 g, 0.13 mol) was added dropwise under a nitrogen atmosphere over 3 hours to an ice cold solution of 4-phenoxyphenyl (25.0 g, 0.13 mol) in 125 ml of carbon disulfide. After the addition, the reaction was stirred at ice bath temperature for 1 hour. The cooling bath was removed and the stirring continued at room temperature overnight. The solvent was removed under reduced pressure. The residual oil was taken up in methylene chloride and the organic solution was washed with brine, dried (MgSO$_4$) and the solvent was removed under reduced pressure to give 37.2 g of a light brown oil. Purification of this material on HPLC using methylene. chloride as an eluent gave 2-bromo-4-phenoxyphenol as a light yellow oil (29.7 g, 85%): IR (film) 3500, 3050, 3020, 1580 and 1470 cm$^{-1}$; ms m/e, 264/266 (m+).

In the same manner as described in Example 1, the title compound was produced from the intermediate of the preceding paragraph as a white crystalline solid after recrystallization of the crude reaction product from diisopropyl ether (4.35 g, 63%), mp 57°–60° C.

Elemental analysis for C $_{17}H_{18}BrNO_3$ Calc'd: C, 56.06; H, 4.98; N, 3.84 Found: C, 55.68; H, 5.01; N, 3.79

EXAMPLE 34

4-Methyl1-piperidinecarboxylic acid 2-bromo-4-phenoxyphenyl ester

In the same manner as described in Example 2, the title compound was produced from the intermediate prepared in paragraph 1 of Example 32 as a white crystalline solid after recrystallization from hexane (5.71 g, 65%), mp 65°–68° C.

Elemental analysis for $C_{19}H_{20}BrNO_3$ Calc'd: C, 58.47; H, 5.16; N, 3.59 Found: C, 58.23; H, 5.05; N, 3.38

EXAMPLE 35

(1,5-Dimethylhexyl)carbamic acid 2-bromo-4-phenoxyphenyl ester

In the same manner as described in Example 2, the title compound was produced from the intermediate prepared in paragraph 1 of Example 32 as a white crystalline solid after recrystallization from hexane (4.26 g, 45%), mp 64°–67° C.

Elemental analysis for $C_{21}H_{26}BrNO_3$ Calc'd: C, 60.00; H, 6.23; N, 3.33 Found: C, 60.06; H, 6.08; N, 3.31

EXAMPLE 36

Hexylcarbamic acid 4-phenoxyphenyl ester

In the same manner as described in Example 1, the title compound was formed in high yield. Recrystallization of the crude reaction mixture from diisopropyl ether gave 2.18 g (26%) of the title compound as a white crystalline solid, mp 57°–59° C.

Elemental analysis for $C_{19}H_{23}NO_3$ Calc'd: C, 72.82; H, 7.40; N, 4.47 Found: C, 72.68; H, 7.17; N, 4.81

EXAMPLE 37

(1,5-Dimethylhexyl)carbamic acid 2-fluoro-4-phenoxyphenyl ester

In the same manner as described in Example 2, the title compound was produced from the intermediate prepared in paragraphs 1 and 2 of Example 28 as a white, waxy solid after recrystallization from hexane (6.40 g, 73%), mp 37°–41° C.

Elemental analysis for $C_{21}H_{26}FNO_3$ Calc'd: C, 70.17; H, 7.29; N, 3.90 Found: C, 70.16; H, 7.17; N, 3.71

EXAMPLE 38

4,4-Dimethyl-1piperidinecarboxylic acid 4-phenoxyphenol ester

In the same manner as described in Example 2, the title compound was produced as a white crystalline solid (4.1 g, 45%), mp 63°–65° C.

Elemental analysis for $C_{20}H_{23}NO_3$ Calc'd: C, 73.82; H, 7.12; N, 4.30 Found: C, 73.86; H, 7.23; N, 4.36

EXAMPLE 39

3-Methyl-1-piperidinecarboxylic acid 4-phenoxyphenyl ester

In the same manner as described in Example 2, the title compound was produced as a white crystalline solid (2.20 g, 26%), mp 41°–43° C.

Elemental analysis for $C_{19}H_{21}NO_3$ Calc'd: C, 73.29; H, 6.80; N, 4.50 Found: C, 73.16; H, 6.66; N, 4.24

EXAMPLE 40

Hexahydro-1H-azepine-1-carboxylic acid 4-phenoxyphenyl ester

In the same manner as described in Example 2, the title compound was produced as a white crystalline solid (4.09 g, 49%), mp 75°–77° C.

Elemental analysis for $C_{19}H_{21}NO_3$ Calc'd: C, 73.29; H, 6.80; N, 4.50 Found: C, 72.97; H, 6.72; N, 4.52

EXAMPLE 41

4-Methyl-1-piperidinecarboxylic acid 2-fluoro-4-phenoxyphenyl ester

In the same manner as described in Example 2, the title compound was produced from the intermediate prepared in paragraphs 1 and 2 of Example 28 as a crystalline solid (3.18 g, 39%), mp 43°–46° C.

Elemental analysis for $C_{19}H_{20}FNO_3$ Calc'd: C, 69.29; H, 6.12; N, 4.25 Found: C, 69.50; H, 6.23; N, 4.26

EXAMPLE 42

4-Ethyl-1-piperidinecarboxylic acid 4-phenoxyphenyl ester

In the same manner as described in Example 2, the title compound was produced as a white crystalline solid (4.76 g, 55%), mp 38°–40° C.

Elemental analysis for $C_{20}H_{23}NO_3$ Calc'd: C, 73.82; H, 7.12; N, 4.30 Found: C, 74.09; H, 7.20; N, 4.33

EXAMPLE 43

1,4-Piperidinedicarboxylic acid 4-ethyl-1-(4phenoxyphenyl) diester

In the same manner as described in Example 2, the title compound was produced as a clear oil (7.18 g, 73%), FAB, MS, m/e 370 (M+H).

Elemental analysis for $C_{21}H_{23}NO_5$ Calc'd: C, 68.28; H, 6.28; N, 3.79 Found: C, 67.67; H, 6.30; N, 4.01

EXAMPLE 44

4-Hydroxy1-piperidinecarboxylic acid 4-phenoxyphenyl ester

A solution of 4-phenoxyphenol (30 g, 0.16 mol) and dimethylaniline (20.4 ml, 0.16 mol) in 200 ml of benzene plus 9 ml of dioxane was added dropwise over 15 minutes under a nitrogen atmosphere to a solution of trichloromethyl chloroformate (9.7 ml, 0.08 mol) in 60 ml of benzene at ice bath temperature. After the addition, the cooling bath was removed and the stirring continued for 24 hours. The reaction mixture was filtered and the filtrate was then added dropwise under a nitrogen atmosphere to a solution of 4-hydroxypiperidine (16.3 g, 0.16 mol) and pyridine (26.1 ml, 0.32 mol) in 150 ml each of benzene, methylene chloride and THF at ice bath temperature. After the addition, the reaction was stirred at ice bath temperature for 3 hours. The cooling bath was removed and the stirring continued overnight. The reaction mixture was diluted with benzene and washed with 1N HCl. The organic solution was separated, dried over anhydrous MgSO4 and the solvent removed under reduced pressure to give 46.4 g of a yellow mushy solid. Purification by HPLC (hexane:EtOAc) gave 13.3 g of a white solid. Recrystallization from diisopropyl ethermethanol gave the title compound as a white crystalline solid (10.4 g, 21%), mp 128°–130° C.

Elemental analysis for $C_{18}H_{19}NO_4$ Calc'd: C, 69.00; H, 6.11; N, 4.47 Found: C, 68.99; H, 6.06; N, 4.43

EXAMPLE 45

4Propyl-1-piperidinecarboxylic acid 4-phenoxyphenyl ester

In the same manner as described in Example 2, the title compound was produced as a white crystalline solid (1.86 g, 21%), mp 68°–70° C.

Elemental analysis for $C_{21}H_{25}NO_3$ Calc'd: C, 74.31; H, 7.42; N, 4.13 Found: C, 74.45; H, 7.44; N, 4.24

EXAMPLE 46

1.4-Piperidinedicarboxylic acid 1-(1-phenoxyphenyl ester)

The material prepared in Example 43 (3.0 g, 8.1 mmol) was dissolved in 50 ml of THF plus 25 ml of water. One equivalent of 1N NaOH was added and the reaction mixture was stirred under a nitrogen atmosphere at room temperature for 24 hours. The THF was removed under reduced pressure. The residue was partitioned between ethyl acetate and water. The aqueous layer was washed two additional times with ethyl acetate. The aqueous layer was acidified with 1N HCl and the product extracted with ethyl acetate. The ethyl acetate solution was dried (anhydrous MgSO4) and the solvent removed under reduced pressure to give 2.34 g of a white solid. Recrystallization from diisopropyl ether-methanol gave the title compound as a white crystalline solid (0.79 g, 28%), mp 140°–141° C.

Elemental analysis for $C_{19}H_{19}NO_5$ Calc'd: C, 66.85; H, 5.61; N, 4.10 Found: C, 66.82; H, 5.61; N, 4.18

EXAMPLE 47

3,3-Dimethyl-1-piperidinecarboxylic acid 4-phenoxyphenyl ester

In the same manner as described in Example 2, the title compound was produced as a white crystalline solid (2.59 g, 29%), mp 57°–60° C.

Elemental analysis for $C_{20}H_{23}NO_3$Calc'd: C, 73.82; H, 7.12; N, 4.30 Found: C, 73.66; H, 7.11; N, 4.36

EXAMPLE 48

4-(Acetyloxy)-1-piperidinecarboxylic acid 4-phenoxyphenyl ester

The material prepared in Example 44 (2.0 g, 6.38 mmol) was dissolved 40 ml of methylene chloride. Potassium carbonate (8.8 g, 63.8 mmol) and acetyl chloride (9.1 ml, 128 mmol) were added and the mixture was stirred under nitrogen atmosphere at room temperature overnight. The reaction mixture was washed with water. The organic solution was then separated, dried (anhydrous MgSO4) and the solvent removed under reduced pressure to give 2.22 g of a white solid. Recrystallization from hexane gave the title compound as a white crystalline solid (1.68 g, 74%), mp 99°–101° C.

Elemental analysis for $C_{20}H_{21}NO_5$ Calc'd: C, 67.59; H, 5.96; N, 3.94 Found: C, 67.74; H, 5.95; N, 4.22

EXAMPLE 49

4-Methyl-1-piperidinecarboxylic acid 2-(methoxycarbonyl)-4-phenoxyphenyl ester A solution of bromine (42 g, 0.26 mol) in 50 ml of carbon disulfide was added under a nitrogen atmosphere over 6 hours to a solution of 4-phenoxyphenol (50 g, 0.27 mol) in 400 ml of carbon disulfide at approximately −5° C. After the addition, the reaction was stirred at approximately 3° C. for 3 hours and then at room temperature for 12 hours. The solvent was removed under reduced pressure. The residue was dissolved in methylene chloride and washed with brine. The organic solution was separated, dried (anhydrous MgSO4) and the solvent removed under reduced pressure to give a light brown oil. To remove the unreacted 4-phenoxyphenol, the material was subjected to HPLC (hexane-methylene chloride). NMR analysis of the isolated material (single spot on TLC) showed it to be a mixture of mono and dibrominated phenols. Distillation of this mixture then gave 2-bromo-4-phenoxyphenol as a clear liquid (44.35 g, 64%), bp 137°–143° C. (2 mm).

Elemental analysis for $C_{12}H_9BrO_2$ Calc'd: C, 54.37; H, 3.42 Found: C, 54.12; H, 3.33 n-Butyl lithium (59 ml of a 1.6 M solution in hexanes, 94.4 mmol) was added dropwise over 30 minutes under a nitrogen atmosphere to a solution of 2-bromo-4-phenoxyphenol (10.0 g, 37.7 mmol) in 50 ml of dry THF at −78° C. After the addition, the solution was stirred at −78° C. for 1 hour. An excess of $CO_2$ was then added through a tube of Drierire ® into the reaction mixture. After the addition, the cooling bath was removed and the stirring continued for 1 hour. The reaction was quenched with 1N HCl. Most of the THF was removed under reduced pressure. The residue was partitioned between 1N HCl and EtOAc. The organic layer was separated, dried (anhydrous $MgSO_4$) and the solvent removed under reduced pressure to give 9.81 g of a light yellow solid. This solid was dissolved in $CH_2Cl_2$ containing a small amount of methanol and the solution extracted with 5% $NaHCO_3$. The organic layer was separated and the aqueous layer extracted two additional times with methylene chloride. The aqueous layer was acidified with 1N HCl and the desired product extracted with methylene chloride. The methylene chloride solution was dried (anhydrous $MgSO_4$) and the solvent removed under reduced pressure to give 2-hydroxy-5-phenoxybenzoic acid as a light yellow solid (7.05 g, 81%), mp 126°–128° C.

Elemental analysis for $C_{13}H_{10}O_4$ Calc'd: C, 67.82; H, 4.38 Found: C, 67.86; H, 4.52

An excess of diazomethane in diethyl ether was added in portions to a solution of 2-hydroxy-5-phenoxybenzoic acid (3.53 g, 15.3 mmol) in 50 ml of methylene chloride. The reaction was monitored by TLC. When all of the acid had been consumed, the reaction mixture was quenched with glacial acetic acid. The reaction mixture was then partitioned with 1N HCl. The organic layer was separated, washed with 5% $NaHCO_3$, dried (anhydrous $MgSO_4$) and the solvent removed under reduced pressure to give 4.08 g of a light brown oil. Purification of this oil on silica gel (230–400 mesh) using hexane-methylene chloride as the eluent gave 2-hydroxy-5-phenoxybenzoic acid methyl ester as a white crystalline solid (3.27 g, 87%), mp 33°–35° C.

Elemental analysis for $C_{14}H_{12}O_4$ Calc'd: C, 68.85; H, 4.95 Found: C, 68.66; H, 4.97

Sodium hydride (0.38 g, 9.93 mmol of a 60% oil dispersion) was added in portions under a nitrogen atmosphere to a solution of 2-hydroxy-5-phenoxybenzoic acid methyl ester (2.0 g, 8.19 mmol) in 30 ml of benzene. The reaction was stirred at room temperature for 30 minutes. 4-Methyl-1-piperidinecarbonyl chloride (1.46 g, 9.03 mmol) was then added and the reaction refluxed for 3.5 hours. The reaction mixture was washed with 1N HCl, dried (anhydrous $MgSO_4$) and the solvent removed under reduced pressure to give 3.38 g of a clear oil. Purification of this oil on 300 g of silica gel (230–400 mesh) using hexane-methylene chloride as the eluent gave 2.71 g of a white crystalline solid. Recrystallization of this solid from diisopropyl ether-hexane then gave the title compound as a white crystalline solid (2.02 g, 67%), mp 67–69 C.

Elemental analysis for $C_{21}H_{23}NO_5$ Calc'd: C, 68.28; H, 6.28; N, 3.79 Found: C, 68.61; H, 6.38; N, 3.88

EXAMPLE 50

2[[(Butylamino)carbonyloxy]-5-phenoxybenzoic acid methyl ester

In the same manner as described in Example 1, the title compound was produced from the intermediate prepared in paragraph 3 of the preceding example as a white crystalline solid after purification by chromatography on silica gel (230–400 mesh) using methylene chloride as the eluent (0.33 g, 58%), mp 53°–56° C.

Elemental analysis for $C_{19}H_{21}NO_5$ Calc'd: C, 66.46; H, 6.16; N, 4.08 Found: C, 66.34; H, 6.21; N, 4.20

EXAMPLE 51

4-(1-Methylethyl)-1-piperidinecarboxylic acid 4-phenoxyphenyl ester

In the same manner as described in Example 2, the title compound was produced as a white crystalline solid (3.02 g, 33%), mp 54°–55° C.

Elemental analysis for $C_{21}H_{25}NO_3$ Calc'd: C, 74.31; H, 7.42; N, 4.13 Found: C, 74.03; H, 7.41; N, 4.00

EXAMPLE 52

8-Azaspiro[4,5]decan-8-carboxylic acid 4-phenoxyphenyl ester

In the same manner as described in Example 2, the title compound was produced as a white crystalline solid (4.16 g, 44%), mp 53°–55° C.

Elemental analysis for $C_{22}H_{25}NO_3$ Calc'd: C, 75.19; H, 7.17; N, 3.99 Found: C, 75.51; H, 7.36; N, 3.94

EXAMPLE 53

1,4-Piperidinedicarboxylic acid 4-dodecyl 1-(4-phenoxyphenyl) diester

Dodecyl alcohol (1.0 ml, 4.4 mmol) was added under a nitrogen atmosphere to a solution of the acid prepared in Example 46 (1.5 g, 4.4 mmol) and 4-dimethylpyridine (0.54 g, 4.4 mmol) in 20 ml of methylene chloride at ice bath temperature. Diisopropylcarbodiimide (650 μl, 4.4 mmol) in 5 ml of methylene chloride was then added dropwise over 15 minutes. After the addition, the reaction was stirred at ice bath temperature for 1 hour and at room temperature for 3 hours. The reaction mixture was washed with 1N HCl, 5% $NaHCO_3$, dried (anhydrous $MgSO_4$) and the solvent removed under reduced pressure to give 2.46 g of residue. Purification of this residue by column chromatography on 250 g of silica gel (230–400 mesh) using methylene chloride as the eluent gave 1.80 g of a white solid. Recrystallization of this solid from hexane gave the title compound as a white crystalline solid (1.13 g, 59% ), mp 35°–37° C.

Elemental analysis for $C_{31}H_{43}NO_5$ Calc'd: C, 73.05; H, 8.50; N, 2.75 Found: C, 73.14; H, 8.79; N, 2.68

EXAMPLE 54

4-Methyl-1-piperidinecarboxylic acid 2-cyano-4-phenoxyphenyl ester

A mixture of the intermediate prepared in paragraph 1 of Example 49 (14.95 g, 56.4 mmol), methyl iodide (17.6 ml, 283 mmol) and potassium carbonate (39 g, 282 mmol) in 150 ml of acetone was stirred under a nitrogen atmosphere at room temperature overnight. The solid was removed by filtration and the flitrate concentrated under reduced pressure to remove the acetone. The residue was partitioned between methylene chloride and water. The organic layer was separated, dried (anhydrous MgSO$_4$) and the solvent removed under reduced pressure to give 15.35 g of a yellow crystalline solid. Recrystallization of this solid from hexane gave 3-bromo-4-methoxybiphenyl ether as a white crystalline solid (10.58 g, 67%), mp 50°-52° C.

Elemental analysis for C$_{13}$H$_{11}$BrO$_2$ Calc'd: C, 55.94; H, 3.97 Found: C, 56.30; H, 3.97 n-Butyl lithium (24 ml of a 1.6 M solution in hexanes; 38.4 mmol) was added dropwise over 30 minutes under a nitrogen atmosphere to a solution at −78° C. of 3-bromo-4-methoxybiphenyl ether (9.0 g, 32.2 mmol) in 250 ml of dry THF. After the addition, the solution was stirred at −78° C. for 3 hours. N-Formylmorpholine (3.9 ml, 38.8 mmol) was then added dropwise over 10 minutes. After the addition, the reaction was stirred at −78° C. for 30 minutes and then at room temperature overnight. The mixture was cooled to ice bath temperature and then 200 ml of 10% NH$_4$Cl was added. The mixture was stirred at ice bath temperature for 30 minutes. The reaction was partitioned between 1N HCl and EtOAc. The organic layer was separated, dried (anhydrous MgSO$_4$) and the solvent removed under reduced pressure to give 7.81 g of a yellow oil. Purification of this oil by HPLC (hexane-methylene chloride) gave 6.02 g of a light yellow crystalline solid. Recrystallization of this solid from diisopropyl etherhexane gave 2-methoxy-5-phenoxybenzaldehyde as a white crystalline solid (4.80 g, 65%), mp 60°-61° C.

Elemental analysis for C$_{14}$H$_{12}$O$_3$ Calc'd: C, 73.67; H, 5.30 Found: C, 73.83; H, 5.27

2-Methoxy-5-phenoxybenzaldehyde (4.5 g, 19.7 mmol) was dissolved in 60 ml of warm methanol. Water (40 ml) was added to this solution followed by the addition of hydroxylamine hydrochloride (2.7 g, 38.9 mmol) and anhydrous sodium acetate (6.5 g, 79.2 mmol). This mixture was then refluxed for 4 hours. The reaction mixture was concentrated under reduced pressure to remove the methanol. The residue was partitioned with ethyl acetate. The ethyl acetate layer was separated, washed five times with water, dried (anhydrous MgSO$_4$) and the solvent removed under reduced pressure to give 2-methoxy-5-phenoxybenzaldehyde oxime as a white crystalline solid (4.70 g, 98%), mp 95°-100° C.

Elemental analysis for C$_{14}$H$_{13}$NO$_3$ Calc'd: C, 69.13; H, 5.39; N, 5.76 Found: C, 69.04; H, 5.35; N, 5.71

Thionyl chloride (11.9 ml, 163 mmol) was added under a nitrogen atmosphere to a suspension of 2-methoxy-5-phenoxybenzaldehyde oxime (3.96 g, 16.3 mmol) in 75 ml of benzene. There was a slight exotherm and the mixture turned yellow. The reaction was heated to reflux temperature over 1 hour and at reflux temperature for an additional hour. The solvent and excess thionyl chloride were removed under reduced pressure to give 2-methoxy-5-phenoxybenzonitrile as a light tan crystalline solid (3.66 g, 100%), mp 88°-89° C.

Elemental analysis for C$_{14}$H$_{11}$NO$_2$ Calc'd: C, 74.65; H, 4.92; N, 6.22 Found: C, 74.67; H, 4.78; N, 6.16

A round bottom flask containing 30 g of pyridinium hydrochloride was put under a nitrogen atmosphere and submerged in an oil bath at 210° C. After the pyridinium hydrochloride melted 2-methoxy-5-phenoxybenzonitrile (3.31 g, 14.7 mmol) was added and the resulting solution stirred at 210° C. (oil bath temperature) for 25 minutes. After cooling to room temperature, the contents of the flask solidified. The solid was partitioned between 1N HCl and ethyl acetate. The ethyl acetate layer was separated, dried (anhydrous MgSO$_4$) and the solvent removed under reduced pressure to give 3.06 g of a brown crystalline solid. Purification of this solid by chromatography on silica gel (230–400 mesh) using ethyl acetate-methylene chloride as an eluent gave 2-hydroxy-5-phenoxybenzonitrile as a white crystalline solid (2.56, 83%), mp 112°-114° C.

Elemental analysis for C$_{13}$H$_9$NO$_2$ Calc'd: C, 73.92; H, 4.30; N, 6.63 Found: C, 74.23; H, 4.47; N, 6.60

4-Methyl-1-piperidinecarbonyl chloride (1.18 ml, 8.01 mmol) was added under a nitrogen atmosphere at room temperature to a solution of 2-hydroxy-5-phenoxybenzonitrile (1.53 g, 7.26 mmol) and 4-dimethylaminopyridine (0.976 g, 7.99 mmol) in 50 ml of benzene and the resulting solution refluxed for 1 hour. The reaction mixture was washed with 1N HCl. The benzene layer was separated, dried (anhydrous MgSO$_4$) and the solvent removed under reduced pressure to give 2.57 g of a white crystalline solid. Rectystallization of this solid from diisopropyl ether-hexane gave the title compound as a white crystalline solid (1.59 g, 65%), mp 54°-58° C.

Elemental analysis for C$_{20}$H$_{20}$N$_2$O$_3$ Calc'd: C, 71.41; H, 5.99; N, 8.33 Found: C, 71.67; H, 5.95; N, 8.38

EXAMPLE 55

4-Methyl-1-piperidinecarboxylic acid 2-(hydroxycarbonyl-4-phenoxyphenyl ester

The ester produced in Example 49 (0.4519 g, 1.22 mmol) was dissolved in 8 ml of THF and the solution put under a nitrogen atmosphere. Water (2 ml) was added followed by the addition of 1.22 ml (1.22 mmol) of 1N NaOH. The solution was refluxed for 21 hours. The reaction was partitioned between ethyl acetate and water. The organic layer was separated. The aqueous layer was acidified with 1N HCl and then extracted three times with ethyl acetate. The ethyl acetate layer was dried (anhydrous MgSO$_4$) and the solvent removed under reduced pressure to give 0.3452 g of a white solid. Recrystallization of this solid from ethyl acetate gave the title compound as a white crystalline solid (0.2094 g, 48%), mp 152° C. with decomposition.

Elemental analysis for C$_{20}$H$_{21}$NO$_5$ Calc'd: C, 67.59; H, 5.96; N, 3.94 Found: C, 67.41; H, 5.82; N, 3.86

EXAMPLE 56

4-(Hydroxymethyl)-1-piperidinecarboxylic acid 4-phenoxyphenyl ester

The acid produced in Example 46 (2.0 g, 5.8 mmol) was dissolved in 20 ml of dry THF. The solution was put under a nitrogen atmosphere and cooled to ice bath temperature. Borane-THF complex (5.8 ml of a 1.0 M solution in THF; 5.8 mmol) was added dropwise to the above solution and the reaction stirred at ice bath temperature for 2 hours. The reaction was quenched with 1N HCl. The THF was removed under reduced pressure and the residue partitioned between ethyl acetate and 1N HCl. The ethyl acetate layer was separated, dried (anhydrous MgSO$_4$) and the solvent removed under reduced pressure to give 1.84 g of a waxy solid. Purification of this solid by chromatography on silica gel (230–400 mesh) using ethyl acetatemethylene chloride as an eluent gave the title compound as a white solid (1.40 g, 74%), mp 71°-74° C.

Elemental analysis for C$_{19}$H$_{21}$NO$_4$ Calc'd: C, 69.71; H, 6.47; N, 4.28 Found: C, 69.46; H, 6.51; N, 4.23

EXAMPLE 57

4-(Bromomethyl)-1-piperidinecarboxylic acid, 4-phenoxyphenyl ester

The ester produced in Example 56 (5.0 g, 15 mmol) and triphenylphosphine (4.0 g, 15 mmol) were dissolved in 100 ml of benzene and the resulting solution put under a nitrogen atmosphere. N-Bromosuccinimide (2.7 g, 15 mmol) was added in portions to the above solution and the reaction stirred at room temperature overnight. The solvent was removed under reduced pressure to give 12.3 g of a brown oil. Purification of this oil by chromatography on 600 g of silica gel (230–400 mesh) using ethyl acetate-hexane as the eluent gave 4.52 g of a white solid. Recrystallization of this solid from diisopropyl ether gave the title compound as a white crystalline solid (4.12 g, 68%), mp 76°–78° C.

Elemental analysis for $C_{19}H_{20}NO_3Br$ Calc'd: C, 58.57; H, 5.17; N, 3.59 Found: C, 58.50; H, 5.12; N, 3.43

EXAMPLE 58

4-Methyl-1-piperidinecarboxylic acid 2-(dodecyloxycarbonyl)-4-phenoxyphenyl ester The acid produced in Example 55 (2.0 g, 5.63 mmol) and 4-dimethyaminopyridine (0.69 g, 5.67 mmol) were dissolved in 40 ml of methylene chloride and the solution put under a nitrogen atmosphere. Dodecyl alcohol (1.2 ml, 5.28 mmol) and diisopropylcarbodiimide (0.88 ml, 5.62 mmol) were added in that order to the above solution and the reaction stirred at room temperature overnight. The reaction was washed with 1N HCl, 5% NaHCO$_3$, dried (anhydrous MgSO$_4$) and the solvent removed under reduced pressure. Purification of the residue (3.71 g) by chromatography on 400 g of silica gel (230–400 mesh) using methylene chloridehexane as the eluent gave the title compound as a white waxy solid (2.70 g, 97%), mp 37°–39° C.

Elemental analysis for $C_{32}H_{45}NO_5$ Calc'd: C, 73.39; H, 8.66; N, 2.68 Found: C, 73.19; H, 8.36; N, 2.64

EXAMPLE 59

4-(Iodomethyl)-1-piperidinecarboxylic acid 4-phenoxyphenyl ester

A solution of the bromide produced in Example 57 (1.0 g, 2.56 mmol) and sodium iodide (3.8 g, 25.6 mmol) in 20 ml of acetone was refluxed for 6 hours and then stirred at room temperature overnight. The reaction mixture was partitioned between ethyl acetate and water. The organic layer was separated, washed with water, dried (anhydrous MgSO$_4$) and the solvent removed under reduced pressure to give 1.07 g of a white solid. Recrystallization of this solid from hexane gave the title compound as a white crystalline solid (0.70 g, 64%), mp 106°–107° C.

Elemental analysis for $C_{19}H_{20}NO_3I$ Calc'd: C, 52.19; H, 4.61; N, 3.20 Found: C, 52.50; H, 4.85; N, 3.12

EXAMPLE 60

4-(Diethylaminomethyl-1-piperidinecarboxylic acid 4-phenoxyphenyl ester

A solution of the bromide (1.3 g, 3.3 mmol) produced in Example 57 in 13 ml of diethylamine was refluxed under a nitrogen atmosphere for 6 days. The diethylamine was removed under reduced pressure to give 1.88 g of a yellow mushy solid. Purification of this solid by chromatography on 150 g of silica gel (230–400 mesh) using hexane-ethyl acetate as the eluent gave 1.01 g of a yellow solid. Recrystallization of the solid from hexane gave the title compound as a white crystalline solid (0.61 g, 48%), mp 69°–70° C.

Elemental analysis for $C_{23}H_{30}N_2O_3$ Calc'd: C, 72.22; H, 7.91; N, 7.32 Found: C, 72.13; H, 8.23; N, 7.24

EXAMPLE 61

Triethyl 1-[(4-phenoxyphenoxy)carbonyl]-4-piperidinemethanaminium iodide

A solution of the product of Example 61 (0.30 g, 0.78 mmol) and ethyl iodide (2.8 ml, 39 mmol) in 30 ml of benzene was refluxed under a nitrogen atmosphere for 48 hours. The solid formed was collected by filtration, rinsed with benzene, hexane and then dried under high vacuum to give the title compound as a white solid (0.41 g, 96%), mp 151°–152° C.

Elemental analysis for $C_{25}H_{35}N_2O_3I$ Calc'd: C, 55.76; H, 6.55; N, 5.20 Found: C, 55.71; H, 6.77; N, 5.09

EXAMPLE 62

4-(Dihexylaminomethyl)-1-piperidinecarboxylic acid 4-phenoxyphenyl ester

A solution of the bromide produced in Example 57 (3.0 g, 7.7 mmol) and dihexylamine (9.0 ml, 38 mmol) in 30 ml of toluene was refluxed under a nitrogen atmosphere for 10 days. The solvent was removed under reduced pressure. Purification of the residue (9.88 g) by chromatography on 400 g of silica gel (230–400 mesh) using hexane-ethyl acetate as the eluent gave the title compound as a light yellow solid (3.63 g, 96%), mp 46°–47° C.

Elemental analysis for $C_{31}H_{46}N_2O_3$ Calc'd: C, 75.26; H, 9.37; N, 5.66 Found: C, 75.61; H, 9.74; N, 5.98

EXAMPLE 63

2-Methyl-1-piperidinecarboxylic acid 4-phenoxyphenyl ester

In the same manner as described in Example 2, the title compound was produced as a white crystalline solid (1.57 g, 19%), mp 68°–70° C.

Elemental analysis for $C_{19}H_{21}NO_3$ Calc'd: C, 73.29; H, 6.80; N, 4.50 Found: C, 73.18; H, 6.86; N, 4.61

EXAMPLE 64

Phenylcarbamic acid 4-phenoxyphenyl ester

In the same manner as described in Example 1, the title compound was produced as a white crystalline solid (4.80 g, 58%) after purification by HPLC (hexane:ethyl acetate) and recrystallization from methylene chloride-isopropyl ether, mp 117°–118° C.

Elemental analysis for $C_{19}H_{15}NO_3$ Calc'd: C, 74.74; H, 4.95; N, 4.59 Found: C, 74.59; H, 4.88; N, 4.38

EXAMPLE 65

Phenylmethylcarbamic acid 4-phenoxyphenyl ester

In the same manner as described in Example 2, the title compound was produced as a white crystalline solid (4.26 g, 50%), mp 103°–104° C.

Elemental analysis for $C_{20}H_{17}NO_3$ Calc'd: C, 75.22; H, 5.36; N, 4.39 Found: C, 75.48; H, 5.56; N, 4.29

EXAMPLE 66

Phenylethylcarbamic acid 4-phenoxyphenyl ester

In the same manner as described in Example 2, the title compound was produced as a white crystalline solid (3.80 g, 43%), mp 93°–94° C.

Elemental analysis for $C_{20}H_{17}NO_3$ Calc'd: C, 75.66; H, 5.75; N, 4.20 Found: C, 76.00; H, 5.83; N, 4.35

EXAMPLE 67

(Z)-9-Octadecenylcarbamic acid 4-phenoxyphenyl ester

In the same manner as described in Example 2, the title compound was produced as a white waxy solid (6.90 g, 53%), mp 39°–43° C.

Elemental analysis for $C_{31}H_{45}NO_3$ Calc'd: C, 77.62; H, 9.46; N, 2.92 Found: C, 77.62; H, 9.61; N, 3.01

In the same manner as described in Example 2, the following compounds can be prepared from 4-phenoxyphenol and the appropriate amine.

(1-methyl-4-phenylbutyl)carbamic acid 4-phenoxyphenyl ester methyl(4-phenylbutyl)carbamic acid 4-phenoxyphenyl ester (11-phenylundecyl)carbamic acid 4-phenoxyphenyl ester

[4-(4-methylphenyl)butyl]carbamic acid 4-phenoxyphenyl ester

[4-(4-chlorophenyl)butyl]carbamic acid 4-phenoxyphenyl ester

[4-(4-methoxyphenyl)butyl]carbamic acid 4-phenoxyphenyl ester

[4-[4-(trifluoromethyl)phenyl]butyl]carbamic acid 4-phenoxyphenyl ester

[4-(3-cyanophenyl)butyl]carbamic acid 4-phenoxyphenyl ester

[4-(2-nitrophenyl)butyl]carbamic acid 4-phenoxyphenyl ester

[4-[(1,1'-biphenyl)-4-yl]butyl]carbamic acid 4-phenoxyphenyl ester

The ability of the compounds of this invention to inhibit the formation of cholesteryl esters and thereby interfere with and prevent assimilation of cholesterol into the lymphatic system and ultimately the blood stream was established by incubating the compounds at 37° C. with a mixture of cholesterol and oleic acid in the presence of buffered cholesterol esterase [(EC 3.1.1.13) Sigma Chemical Company, St. Louis, Mo., USA, No. C-1892, from bovine pancreas] and measuring the amount of ester formed, according to the procedure of Field, J. of Lipid Research, 25 389 (1984). The concentration of test compound that inhibits one-half of the ester formation ($IC_{50}$, $\mu M$) is given in the following Table.

The in vivo cholesterol absorption studies were conducted in normal rats by oral administration of the compound being tested in propylene glycol and olive oil followed by oral administration of [4-$^{14}$C] cholesterol in propylene glycol and olive oil, otherwise following the procedure of Cayen et al., J. Lipid Res. 20 162 (1979). The serum radioactivity was measured at six hours after dosing. The results of this study are reported in the following Table, where available, as percent decrease compared to control and in terms of the effective dose ($ED_{50}$) inhibiting fifty-percent of the absorption of the control animals.

TABLE

| Test Compound Example | In Vitro $IC_{50}$ ($\mu M$) | In Vivo Decrease in [$^{14}$C] Cholesterol Absorption |
|---|---|---|
| 1 | 2 | 82% decrease at 100 mg/kg $ED_{50}$ = 24 mg/kg |
| 2 | 0.13 | 82% decrease at 100 mg/kg $ED_{50}$ = 24 mg/kg |
| 3 | 16 | 70% decrease at 10 mg/kg $ED_{50}$ = 6 mg/kg |
| 4 | 5 | 89% decrease at 100 mg/kg $ED_{50}$ = 13 mg/kg |
| 5 | 33 | |
| 6 | 55 | |
| 7 | 85 | |
| 8 | 0.2–0.06 | 90% decrease at 65 mg/kg $ED_{50}$ = 10 mg/kg |
| 9 | >100 | 40% decrease at 100 mg/kg |
| 10 | 1.1 | 74% decrease at 65 mg/kg $ED_{50}$ = 14 mg/kg |
| 11 | 20 | |
| 12 | 0.3 | 43% decrease at 65 mg/kg |
| 13 | 6.7 | |
| 14 | 9.3 | |
| 15 | 17.5 | 76% decrease at 100 mg/kg |
| 16 | >100 | |
| 17 | 13.3 | |
| 18 | 16.5 | |
| 19 | 5.4 | |
| 20 | 7.6 | 27% decrease at 65 mg/kg |
| 21 | 6.1 | |
| 22 | 20% inhibition at 30 $\mu M$; plateau prior to reaching $IC_{50}$ | |
| 23 | 0.27 | 43% decrease at 65 mg/kg |
| 24 | 5.6 | |
| 25 | 0.17 | 61% decrease at 65 mg/kg |
| 26 | 2.9 | |
| 27 | 7.1 | |
| 28 | 1.9 | |
| 29 | 13 | |
| 30 | 1.2 | 83% decrease at 65 mg/kg |
| 31 | 26 | |
| 32 | >100 | |
| 34 | 0.31 | 57% decrease at 65 mg/kg |
| 36 | 1.7 | |
| 37 | 1.4 | |
| 38 | 0.23 | 86% decrease at 50 mg/kg |
| 39 | 0.88 | 73% decrease at 50 mg/kg |
| 40 | 19 | |
| 41 | 0.03 | 73% decrease at 50 mg/kg |
| 42 | 0.05 | 81% decrease at 50 mg/kg |
| 43 | 4.5 | 60% decrease at 50 mg/kg |
| 44 | 1.9 | 49% decrease at 50 mg/kg |
| 45 | 0.07 | 41% decrease at 10 mg/kg |
| 46 | 44 | 55% decrease at 100 mg/kg |
| 47 | 1.6 | 67% decrease at 20 mg/kg |
| 48 | 0.54 | 41% decrease at 50 mg/kg |
| 49 | 0.34 | 28% decrease at 50 mg/kg |
| 50 | 5.1 | |
| 51 | 0.25 | 66% decrease at 20 mg/kg |
| 52 | 0.75 | 78% decrease at 50 mg/kg |
| 53 | >100 | 44% decrease at 100 mg/kg |
| 54 | 0.44 | 36% decrease at 50 mg/kg |
| 55 | 31.3 | 16% decrease at 50 mg/kg |
| 56 | 2.1 | |
| 57 | 0.08 | 87% decrease at 50 mg/kg |
| 58 | 0.34 | 37% decrease at 50 mg/kg |
| 59 | 0.27 | |
| 60 | >100 | 49% decrease at 50 mg/kg |
| 61 | >100 | 33% decrease at 50 mg/kg |
| 62 | 15 | |
| 63 | >100 | 68% decrease at 50 mg/kg |
| 67 | 626 | 49% decrease at 100 mg/kg |

Thus, the compounds of this invention axe useful in the treatment of high serum cholesterol levels and associated disease states such as coronary heart disease, atherosclerosis, familial hypercholesterolaemia hyperlipaemia and similar disease states. As such, they may be administered to a hypercholesterolaemic patient, orally or parenterally, in an amount sufficient to reduce serum cholesterol concentrations to the desired level. The dosage regimen for therapeutic use of the anti-hypercholesterolaemic agents of this invention will vary with the route of administration, size and age of the person under treatment, as well as the severity of the dysfunction under treatment. Therefore, the treatment must be individualized for the patient under guidance of the attending physician.

The compounds of this invention may be administered by conventional oral or parenteral routes as solids, liquids or isotonic solutions. Conventional adjuvants known to the art may be combined with the compounds to provide compositions and solutions for administration purposes, although it is considered desirable and feasible to use the compounds neat or pure without additives other than for the purpose of providing suitable pharmaceutically acceptable solid or liquid dosage units.

What is claimed is:

1. A compound of the formula:

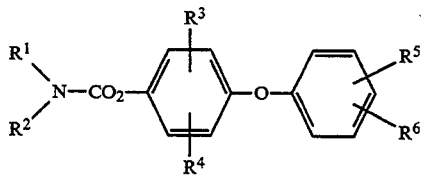

in which
   $R^1$ is branched or straight chain, saturated or unsaturated alkyl of 4 to 20 carbon atoms, cycloalkyl of 3 to 8 carbon atoms, 1-adamantyl, 2-adamantyl, 3-noradamantyl, 3-methyl-1-adamantyl, 1-fluorenyl, 9-fluorenyl, cycloalkylalkyl where the cycloalkyl moiety has 3 to 8 carbon atoms and the alkyl moiety has 1 to 6 carbon atoms, phenyl, substituted phenyl where the substituents are alkyl of 1 to 6 carbon atoms, alkoxy of 1 to 6 carbon atoms, halo, nitro, cyano or trifluoromethyl, phenylalkyl of 7 to 26 carbon atoms or substituted phenylalkyl, where the alkyl moiety is 1 to 20 carbon atoms and the substituent on the benzene ring is alkyl of 1 to 6 carbon atoms, alkoxy of 1 to 6 carbon atoms, halo, nitro, cyano, trifluoromethyl or phenyl;
   $R^2$ is hydrogen or alkyl of 1 to 6 carbon atoms; and
   $R^3$, $R^4$, $R^5$ and $R^6$ are, independently, hydrogen, branched or straight chain alkyl of 1 to 6 carbon atoms, alkoxy of 1 to 6 carbon atoms, halo, nitro, cyano, perhaloalkyl of 1 to 6 carbon atoms, alkoxycarbonyl of 2 to 16 carbon atoms or hydroxycarbonyl.

2. A compound of the formula:

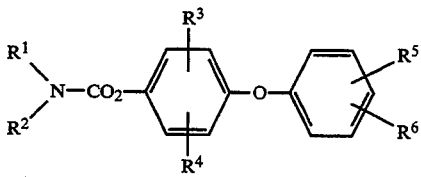

in which
   $R^1$ is cycloalkyl of 3 to 8 carbon atoms, 1-adamantyl, 2-adamantyl, 3-noradamantyl, 3-methyl-1-adamantyl, 1-fluorenyl, 9-fluorenyl, cycloalkylalkyl where the cycloalkyl moiety has 3 to 8 carbon atoms and the alkyl moiety has 1 to 6 carbon atoms, phenyl, substituted phenyl where the substituents are alkyl of 1 to 6 carbon atoms, alkoxy of 1 to 6 carbon atoms, halo, nitro, cyano or trifluoromethyl, phenylalkyl of 7 to 26 carbon atoms or substituted phenylalkyl, where the alkyl moiety is 1 to 20 carbon atoms and the substituent on the benzene ring is alkyl of 1 to 6 carbon atoms, alkoxy of 1 to 6 carbon atoms, halo, nitro, cyano, trifluoromethyl or phenyl;
   $R^2$ is hydrogen or alkyl of 1 to 6 carbon atoms; and
   $R^3$, $R^4$, $R^5$ and $R^6$ are, independently, hydrogen, branched or straight chain alkyl of 1 to 6 carbon atoms, alkoxy of 1 to 6 carbon atoms, halo, nitro, cyano, perhaloalkyl of 1 to 6 carbon atoms, alkoxycarbonyl of 2 to 16 carbon atoms or hydroxycarbonyl.

3. A compound of the forumla:

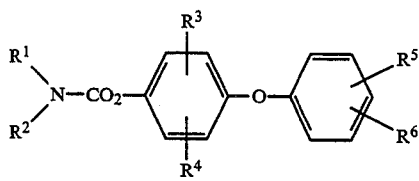

in which
   $R^1$ is cycloalkyl of 4, 5, 6 or 7 carbon atoms, cycloalkylalkyl of 6 to 8 carbon atoms, phenylalkyl of 7 to 26 carbon atoms;
   $R^2$ is hydrogen, methyl or ethyl; and
   $R^3$, $R^4$, $R^5$ and $R^6$ are, independently, hydrogen, alkyl of 1 to 6 carbon atoms, alkoxy of 1 to 6 carbon atoms, nitro, halo, alkoxycarbonyl of 2 to 16 carbon atoms, hydroxycarbonyl, cyano or trihalomethyl.

4. A compound of the formula:

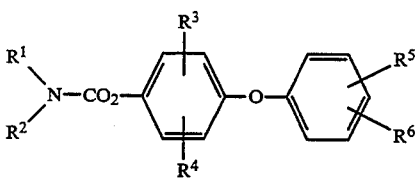

in which
   $R^1$ is branched or straight chain alkyl of 4 to 20 carbon atoms, cycloalkyl of 4, 5, 6 or 7 carbon atoms, cycloalkylalkyl of 6 to 8 carbon atoms, phenylalkyl of 7 to 26 carbon atoms;
   $R^2$ is hydrogen, methyl or ethyl; and
   $R^3$, $R^4$, $R^5$ and $R^6$ are, independently, hydrogen, alkyl of 1 to 6 carbon atoms, alkoxy of 1 to 6 carbon atoms, nitro, halo, alkoxycarbonyl of 2 to 16 carbon atoms, hydroxycarbonyl, cyano or trihalomethyl.

5. The compound of claim 1 which is butylcarbamic acid 4-phenoxyphenyl ester.

6. The compound of claim 2 which is (4-phenylbutyl)-carbamic acid 4-phenoxyphenyl ester.

7. The compound of claim 1 which is (1,5-dimethylhexyl)carbamic acid 4-phenoxyphenyl ester.

8. The compound of claim 1 which is octylcarbamic acid 4-phenoxyphenyl ester.

9. The compound of claim 2 which is cyclohexylcarbamic acid 4-phenoxyphenyl ester.

10. The compound of claim 2 which is cyclohexylmethylcarbamic acid 4-phenoxyphenyl ester.

11. The compound of claim 2 which is tricyclo[3.3.1.1(3,7)dec-1-yl-carbamic acid 4-phenoxyphenyl ester.

12. The compound of claim 1 which is (1,1,3,3-tetramethylbutyl)carbamic acid 4-phenoxyphenyl ester.

13. The compound of claim 1 which is (1-ethylpentyl)carbamic acid 4-phenoxyphenyl ester.

14. The compound of claim 1 which is (1,3-dimethylbutyl)carbamic acid 4-phenoxyphenyl ester.

15. The compound of claim 1 which is butylcarbamic acid 4-(4-methylphenoxy)phenyl ester.

16. The compound of claim 1 which is butylcarbamic acid 4-(4-nitrophenoxy)phenyl ester.

17. The compound of claim 1 which is butylcarbamic acid 4-(4-chlorophenoxy)phenyl ester.

18. The compound of claim 1 which is butylcarbamic acid 2,6-dimethyl-4-(4-methylphenoxy)phenyl ester.

19. The compound of claim 1 which is (1,5-Dimethylhexyl)carbamic acid 4-(4-methylphenoxy)phenyl ester.

20. The compound of claim 1 which is (1-methylhexyl)carbamic acid 4-phenoxyphenyl ester.

21. The compound of claim 1 which is (1,5-dimethylhexyl)carbamic acid 4-(4-chlorophenoxy)phenyl ester.

22. The compound of claim 1 which is butylcarbamic acid 2-fluoro-4-phenoxyphenyl ester.

23. The compound of claim 1 which is butylcarbamic acid 4-(4-methoxyphenoxy)phenyl ester.

24. The compound of claim 1 which is (1,5-dimethylhexyl)carbamic acid 4-(4-methoxyphenoxy)phenyl ester.

25. The compound of claim 1 which is butylcarbamic acid 4-(4-tertbutylphenoxy)phenyl ester.

26. The compound of claim 1 which is butylcarbamic acid 2-bromo-4-phenoxyphenyl ester.

27. The compound of claim 1 which is (1,5-dimethylhexyl)carbamic acid 2-bromo-4-phenoxyphenyl ester.

28. The compound of claim 1 which is hexylcarbamic acid 4-phenoxyphenyl ester.

29. The compound of claim 1 which is (1,5-dimethylhexyl)carbamic acid 2-fluoro-4-phenoxyphenyl ester.

30. The compound of claim 1 which is 2-[[(butylamino)carbonyl]oxy]-5-phenoxybenzoic acid methyl ester.

31. The compound of claim 2 which is phenylcarbamic acid 4-phenoxyphenyl ester.

32. The compound of claim 2 which is phenylmethylcarbamic acid 4-phenoxyphenyl ester.

33. The compound of claim 2 which is phenylethylcarbamic acid 4-phenoxyphenyl ester.

34. The compound of claim 1 which is (Z)-9-octadecenylcarbamic acid 4-phenoxyphenyl ester.

35. A pharmaceutical composition comprising a cholesterol ester hydrolase inhibiting amount of a compound of the formula:

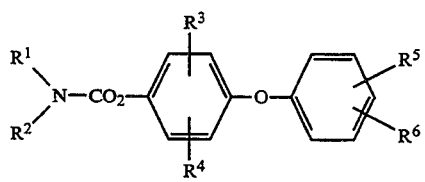

in which
R$^1$ is branched or straight chain, saturated or unsaturated alkyl of 4 to 20 carbon atoms, cycloalkyl of 3 to 8 carbon atoms, 1-adamantyl, 2-adamantyl, 3-noradamantyl, 3-methyl-1-adamantyl, 1-fluorenyl, 9-fluorenyl, cycloalkylalkyl where the cycloalkyl moiety has 3 to 8 carbon atoms and the alkyl moiety has 1 to 6 carbon atoms, phenyl, substituted phenyl where the substituents are alkyl of 1 to 6 carbon atoms, alkoxy of 1 to 6 carbon atoms, halo, nitro, cyano or trifluoromethyl, phenylalkyl of 7 to 26 carbon atoms or substituted phenylalkyl, where the alkyl moiety is 1 to 20 carbon atoms and the substituent on the benzene ring is alkyl of 1 to 6 carbon atoms, alkoxy of 1 to 6 carbon atoms, halo, nitro, cyano, trifluoromethyl or phenyl;

R$^2$ is hydrogen or alkyl of 1 to 6 carbon atoms;

R$^3$, R$^4$, R$^5$ and R$^6$ are, independently, hydrogen, branched or straight chain alkyl of 1 to 6 carbon atoms, alkoxy of 1 to 6 carbon atoms, halo, nitro, cyano, perhaloalkyl of 1 to 6 carbon atoms, alkoxycarbonyl of 2 to 16 carbon atoms or hydroxycarbonyl.

36. The composition of claim 35 in which said compound is (4-phenylbutyl)carbamic acid 4-phenoxyphenyl ester.

37. A process for reducing cholesterol absorption in a mammal in need of reduced serum cholesterol levels which comprises administering orally or parenterally, an amount of a compound of the following formula sufficient to reduce plasma cholesterol concentration:

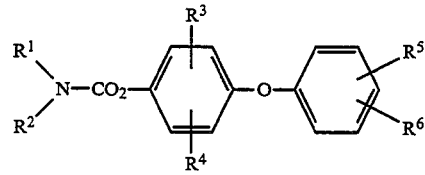

in which
R$^1$ is branched or straight chain, saturated or unsaturated alkyl of 4 to 20 carbon atoms, cycloalkyl of 3 to 8 carbon atoms, 1-adamantyl, 2-adamantyl, 3-noradamantyl, 3-methyl-1-adamantyl, 1-fluorenyl, 9-fluorenyl, cycloalkylalkyl where the cycloalkyl moiety has 3 to 8 carbon atoms and the alkyl moiety has 1 to 6 carbon atoms, phenyl, substituted phenyl where the substituents are alkyl of 1 to 6 carbon atoms, alkoxy of 1 to 6 carbon atoms, halo, nitro, cyano or trifluoromethyl, phenylalkyl of 7 to 26 carbon atoms or substituted phenylalkyl, where the alkyl moiety is 1 to 20 carbon atoms and the substituent on the benzene ring is alkyl of 1 to 6 carbon atoms, alkoxy of 1 to 6 carbon atoms, halo, nitro, cyano, trifluoromethyl or phenyl;

R$^2$ is hydrogen or alkyl of 1 to 6 carbon atoms; and

R$^3$, R$^4$, R$^5$ and R$^6$ are, independently, hydrogen, branched or straight chain alkyl of 1 to 6 carbon atoms, alkoxy of 1 to 6 carbon atoms, halo, nitro, cyano, perhaloalkyl of 1 to 6 carbon atoms, alkoxycarbonyl of 2 to 16 carbon atoms or hydroxycarbonyl and a pharmaceutically acceptable carrier therefor.

38. The process of claim 37 in which said compound is (4-phenylbutyl)carbamic acid 4-phenoxyphenyl ester.

* * * * *